United States Patent [19]

Goudie

[11] 4,198,519

[45] Apr. 15, 1980

[54] ANTI-INFLAMMATORY COMPOUNDS

[75] Inventor: Alexander C. Goudie, Harlow, England

[73] Assignee: Beecham Group Limited, Great Britain

[21] Appl. No.: 952,390

[22] Filed: Oct. 18, 1978

Related U.S. Application Data

[63] Continuation of Ser. No. 815,645, Jul. 14, 1977, abandoned.

[30] Foreign Application Priority Data

Jul. 30, 1976 [GB] United Kingdom ............... 31852/76

[51] Int. Cl.$^2$ ................. C07D 333/24; C07D 333/16; A61K 31/39
[52] U.S. Cl. ....................................... 549/70; 549/71; 549/72; 424/275
[58] Field of Search ......... 260/332.3 C, 517, 332.2 A, 260/332.2 R

[56] References Cited

U.S. PATENT DOCUMENTS

| | | | |
|---|---|---|---|
| 3,655,693 | 4/1972 | Harrington | 260/332.3 |
| 3,696,122 | 10/1972 | Harrington | 260/332.3 |
| 3,832,354 | 8/1974 | Gadient et al. | 260/332.3 |

*Primary Examiner*—Alan Siegel
*Attorney, Agent, or Firm*—Jacobs & Jacobs

[57] ABSTRACT 4-(Thien-2-oyl- and thien-3-oylphenyl)pentan-2-ones and 4-(thien-2-oyl- and thien-3-oylphenyl)butan-2-ones, the corresponding pentan-2-ols and butan-2-ols, and esters of the latter alkanols are anti-inflammatory agents. The compounds, of which 4-[4-(2-thienoyl)-phenyl]pentan-2-one is a representative embodiment, can be prepared by acylation of the corresponding 4-phenylpentan-2-one, 4-phenylbutan-2-one, or an ester of the corresponding pentan-2-ol or butan-2-ol, with a thienylcarboxylic acid, or by acylation of a 4-(4-carboxyphenyl)pentan-2-one, 4-(4-carboxyphenyl)butan-2-one or an ester of the corresponding pentan-2-ol or butan-2-ol with thiophene, optionally in either case with subsequent reduction of the resultant alkanone and with optional esterification of the resultant alkanol.

20 Claims, No Drawings

ANTI-INFLAMMATORY COMPOUNDS

CROSS-REFERENCE

This is a continuation of Ser. No. 815,645 filed July 14, 1977, now abandoned.

The present invention relates to thiophene derivatives, to their preparation and to compositions containing them.

Acidic anti-inflammatory agents such as suprofen tend to suffer from gastro-intestinal side effects. Furthermore such compounds require somewhat long synthetic sequences for production. Suprofen has the formula (O):

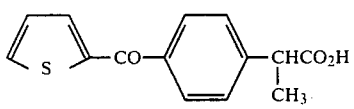

and has been described in Arzneim. Forschung, 25 (11), 1975 and U.K. Pat. No. 1,446,239. A group of non-acid anti-inflammatory agents has now been discovered which show a reduced propensity to cause side effects such as gastro-intestinal irritancy and which are prepared by a conveniently short synthetic sequence.

Accordingly the present invention provides the compounds of the formula (I):

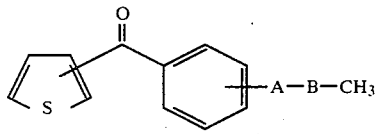

wherein A is a —CHRCH$_2$— or —CR═CH— group where R is a hydrogen atom or a methyl group and B is a CO, CHOH or CHOCOR$^1$ group where R$^1$ is a group such that HO.COR$^1$ is a pharmaceutically acceptable organic acid of up to 12 carbon atoms.

Suitably R$^1$ is a hydrocarbon group such as an alkyl, alkenyl, aryl, aralkyl or like group optionally substituted by alkoxyl, carboxyl, carboxamide, hydroxyl, acyloxy, amino, or salted amino, acylamino, alkylamino, dialkylamino or the like. More suitably R$^1$ is such a group which contains up to 8 carbon atoms.

Preferred groups R$^1$ include the phenyl group, alkyl groups of 1-4 carbon atoms, alkyl groups of 1-4 carbon atoms substituted by a phenyl group, or one of these groups substituted by hydroxyl, acetoxyl, methoxyl, acetamido, amino, salted amino, C$_{1-4}$ alkylamino, di-C$_{1-4}$ alkylamino, carboxyl or the like groups.

Particularly suitable groups R$^1$ include alkyl groups of 1-4 carbon atoms such as the methyl, ethyl, and n-propyl groups. Other groups include the phenyl, benzyl, phenylethyl, acetoxymethyl, methoxymethyl, hydroxymethyl, aminomethyl, 2-acetoxyphenyl, 4-methoxyphenyl, 3,4-dimethoxyphenyl, 3,4,5-trimethoxyphenyl or the like groups.

Aptly B is a CO, CHOH or CHOCOR" group where R" is an alkyl group of 1-4 carbon atoms.

Most suitably the phenyl moiety is 1-4 disubstituted as such compounds are particularly conveniently synthesised as hereinafter described.

Thus particularly suitable compounds of the formula (I) include those of the formulae (II) and (III):

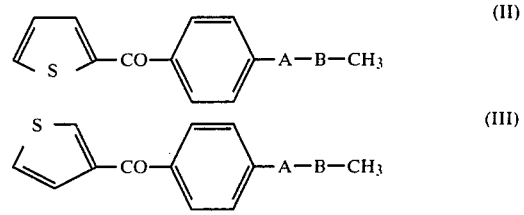

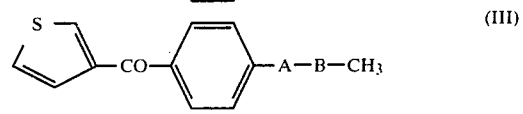

wherein A and B are as defined in relation to formula (I).

Favoured values for the group B in the compounds of the formulae (I), (II) and (III) include the CO and CHOH groups.

A particularly favoured value for the group A in the compounds of the formulae (I), (II) and (III) includes the —CHCH$_3$CH$_2$— group.

Thus further particularly suitable compounds of this invention include those of the formula (IV) and (V):

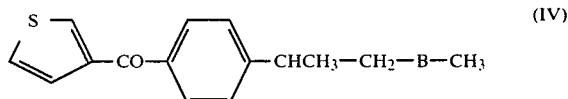

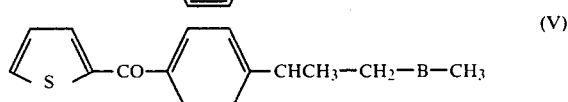

wherein B is as defined in relation to formula (I).

More suitably B the compounds of the formulae (IV) and (V) is a CO, CHOH or CHOCOR$^1$ group.

Yet more favourably B in the compounds of the formulae (IV) and (V) is a CO or CHOH group.

Preferably B in the compounds of the formulae (IV) and (V) is a CO group.

Those compounds of this invention which contain a chiral center may be in the form of R or S isomers or mixtures thereof such as the R,S— form about that center.

Those compounds in which the group A is a CHCH$_3$CH$_2$ group more suitably have the S— or R,S— conformation about the chiral center as the S— compounds are more potent anti-inflammatory agents than the corresponding R— compounds.

The present invention also provides a pharmaceutical composition which comprises a compound of the formula (I) and a pharmaceutically acceptable carrier.

Normally the composition of this invention is adapted for oral administration.

The composition may be presented as any conventional dosage form such as tablets, capsules, sachets of reconstitutable powder or the like. Most suitably the composition is in the form of a unit dose containing 20-600 mg of a compound of the invention, e.g. 50 to 400 mg. Such compositions may be administered once or more times per day so that the total daily dose for a 70 kg adult will be in the order of 40-1200 mg, for example 100-600 mg.

The compositions may be prepared in conventional manner by mixing, filling, tabletting and the like and the compositions may contain conventional excipients such as lubricants, disintegrants, binders, fillers, colouring agents, flavours and the like. The compositions may be formulated in known manner as described for such known anti-inflammatory agents as indomethacin, naproxen, ketoprofen, phenylbutazone or the like.

The present invention provides a process for the preparation of the compounds of the formula (I) which process comprises:

(a) the acylation of a compound of the formula (VI):

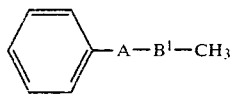

(VI)

wherein $B^1$ is a group within B as defined in relation to formula (I) but excluding the CHOH group with an acylating derivative of a thienylcarboxylic acid; and thereafter if desired reducing the side chain carboxyl group of a compound wherein $B^1$ is a CO group:

(b) the acylation of thiophene with an acylating derivative of the acid of the formula (VII):

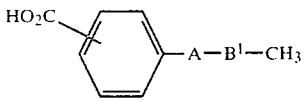

(VII)

wherein $B^1$ is as defined in relation to formula (VI) and thereafter if desired reducing the side chain carboxyl group of a compound wherein $B^1$ is a CO group and thereafter if desired acylating the resulting hydroxyl group with an acylating derivative of a lower alkyl carboxylic acid.

Normally the aromatic acylation is brought about under conventional Friedel Craft acylating conditions, for example by using an acid chloride in the presence of a Lewis acid such as aluminium chloride or antimony chloride in an inert solvent such as carbon disulphide or methylene chloride.

Most suitably the reaction is performed upon a compound of the formula (VI) or (VII) wherein $B^1$ is a CO group.

Those compounds of the invention wherein B is a CHOH group may be prepared by reducing the corresponding compound wherein B is a CO group using sodium borohydride in a solvent such as ethanol or by using lithium aluminium hydride in a solvent such as diethyl ether followed by regeneration of the diaryl ketone using manganese dioxide in an inert solvent such as benzene.

Process (a) is generally used to provide the parasubstituted compounds of the formulae (II) and (III). Process (b) is generally used to provide the 2-thienyl derivatives within formula (I). It will be appreciated that such short processes leading to compounds of the invention are very convenient.

The following Examples illustrate the invention:

EXAMPLE 1

4-[4'-(2'-Thienoyl)-phenyl]-pentan-2-one

To a stirred mixture of aluminium chloride (39 g) in carbon disulphide (150 ml) at 0° C. was added dropwise over 1 hour a mixture of 4-phenyl-pentan-2-one (15 g) and thienyl-2-carboxylic acid chloride (12.8 g). After the resulting dark solution had been left at room temperature overnight, the top layer was decanted off and the lower, more viscous layer was poured carefully onto cold water (about 500 ml). The crude product was extracted into chloroform (3×150 ml), washed with dilute sodium bicarbonate solution (200 ml), dried ($Na_2SO_4$), concentrated by evaporation under reduced pressure and distilled (b.p. 190°/0.08 mm). The residual oil crystallised from ethyl acetate/petrol to give pure 4-[4'-(2'-thienoyl)-phenyl]-pentan-2-one, m.p. 60°–1° C.

EXAMPLE 2

4-[4'-(2'-Thienoyl)-phenyl]-butan-2-one

The procedure of Example 1 was used except that benzyl acetone was used in place of the 4-phenylpentan-2-one. The initially produced somewhat crude product was crystallised from carbon tetrachloride/hexane to give pure 4-[4'-(2'-thienoyl)-phenyl]-butan-2-one, m.p. 77°–78° C.

EXAMPLE 3

4-[4'-(3'-Thienoyl)-phenyl]-butan-2-one

To a stirred mixture of 3-thienoyl chloride (3.0 g) and benzyl acetone (3.0 g) at 0° C. in methylene chloride (50 ml) was added dropwise over 30 minutes antimony pentachloride (3.3 ml). After the reaction mixture had been left at 0° C. for a further 30 minutes and then at room temperature for 3 hours, more antimony pentachloride (3.3 ml) was added dropwise and then the amber solution was left for 1 hour at room temperature before being poured onto cold. dilute aqueous hydrochloric acid (about 50–60 ml). The aqueous layer was separated, washed with chloroform (2×100 ml) and then the combined organic layer was washed successively with dilute aqueous sodium bicarbonate (about 100 ml) and water (about 100 ml), dried ($Na_2SO_4$) and concentrated by evaporation under reduced pressure. The crude oil (4.4 g) was chromatographed on silica using ether/40°–60° petrol as eluant to afford a pale yellow oil which slowly solidified on standing (1.1 g) to a pale amber coloured solid. This material was rechromatographed to yield a colourless solid (400 mg). Recrystallisation of this solid from ether/pentane gave analytically pure 4-[4'-(3'-thienoyl)-phenyl]-butan-2-one, m.p. 63°–4° C.

EXAMPLE 4

S-4-[4'-(2'-Thienoyl)-phenyl]-pentan-2-one

To a stirred mixture of aluminium trichloride (24.45 g) in carbon disulphide (95 ml) at 0° C. was added dropwise over 1 hour a mixture of S-4-phenyl-pentan-2-one (9.4 g) and thienyl-2-carboxylic acid chloride (8.02 g). After the resulting dark solution had been stirred for 24 hours at room temperature, the top layer was decanted off and the lower viscous layer was poured carfully into ice cold dilute hydrochloric acid (about 300 ml). The crude product was extracted into chloroform (3×100 ml), washed with dilute sodium bicarbonate solution (120 ml), dried ($Na_2SO_4$), concentrated by evaporation under reduced pressure and distilled at 176°–178°/0.08 mm to yield a dark oil (9 g). This was chromatographed on alumina using gradient elution with ether and hexane as eluant. The resultant analytically pure S-4-[4'-(2'-thienoyl)-phenyl]-pentan-2-one (5.9 g) had an optical rotation $\alpha_D{}^{18.5} = -76.53$ (benzene).

S-4-phenyl-pentan-2-one was prepared from S-3-phenylbutyric acid ($[\alpha]_D{}^{18} = -60.05°$ in benzene by the method of H. Rupe, Annelen 1901, 369, 311) via its acid chloride by the following method.

Methyl lithium (100 ml of a 2 M solution in ether: 0.2 mole) was added dropwise at 0° C. to cuprous iodide (19 g: 0.1 mole) in dry ether (60 ml) under nitrogen. The solution was then stirred for 10 minutes at 0° C., cooled to −65° and S-3-phenyl-butyroyl chloride (from 4.93 g (0.03 mole) of S-3-phenyl-butyric acid and 10 ml of oxalyl chloride) in dry ether (60 ml) was added slowly. After 15 minutes at −65°, methanol (33 ml) was added dropwise and when the resulting mixture reached −30° C. dilute hydrochloric acid was used to neutralise the solution. After filtration through Kieselguhr, the ether layer was separated and the aqueous layer further extracted with ether. The combined organic layer was then washed with water, dilute aqueous sodium bicarbonate, dried ($Na_2SO_4$), concentrated and distilled to afford pure S-4-phenyl-pentan-2-one (4.1 g), b.p. 110°/11 mm: $[\alpha]_D^{18} = -74.5°$ (benzene).

EXAMPLE 5

R-4-[4'-(2'-Thienoyl)-phenyl]-pentan-2-one

This was prepared following the procedure of Example 4 except that R-4-phenyl-pentan-2-one was used as starting material. Pure R-4-[4'-(2'-thienoyl)-phenyl]-pentan-2-one, was obtained, $[\alpha]_D^{18.5} = +72.08$ (benzene).

R-4-phenyl-pentan-2-one was prepared from R-3-phenylbutyric acid ($[\alpha]_D^{23.3} = 57.12°$ in benzene by the method of A. Weidler and G. Bergson, Acta. Chem. Scand., 1964, 18, 1484) via its acid chloride as follows.

A mixture of ethanol (1.7 ml) and carbon tetrachloride (0.34 ml) was added dropwise to dry magnesium (5.33 g). After the exothermic reaction had subsided, ether (35 ml) was added cautiously. Diethyl malonate (35.56 g), ether (35 ml) and ethanol (17.5 ml) were added at such a rate as to maintain reflux which was then continued overnight. To the resulting stirred solution was added dropwise R-3-phenyl-butyroyl chloride (from 28.29 g of R-3-phenyl-butyric acid and oxalyl chloride) in ether (100 ml) to maintain reflux which was then continued for a further hour after addition. After acidification with dilute hydrochloric acid the aqueous layer was extracted with ether and then the combined organic layer washed with water and concentrated. Treatment of the resulting crude oil with dimethyl sulphoxide (45 ml) and water (7 ml) at 140° for 5 hours gave, after work-up in the usual manner, pure R-4-phenyl-pentan-2-one (24.7 g), b.p. 110°/11 mm: $[\alpha]_D^{20.0} = +73.0$ (benzene).

EXAMPLE 6

Composition

Hard gelatin capsules may each be filled with a mixture of the compound of Example 1 (100 mg) and magnesium stearate (5 mg).

EXAMPLE 7

Pharmacology

The compound of Example 1 showed good activity on the reduction of carrageenin induced oedema test at 10 mg/kg. At 10 mg/kg the compound of Example 1 did not cause severe irritation to the stomachs of the test animals. When tested on the phenylquinone induced writhing test the compound of Example 1 had an $ED_{50}$ of 4.2 mg/kg (c.f. 0.78 for suprofen).

The compound of Example 4 produced a 47% inhibition of oedema in the carrageenin test at 125 mg/kg and 52% at 25 mg/kg. On this test the compound of Example 5 produced a 36% inhibition at 125 mg/kg but only 14% at 25 mg/kg.

What we claim is:

1. A compound of the formula:

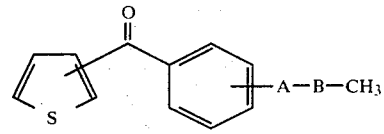

wherein A is —CHRCH$_2$— or —CR=CH— in which R is hydrogen or methyl and B is CO, CHOH or CHOCOR$^1$ wherein R$^1$ is phenyl, alkyl of 1 to 4 carbon atoms, alkyl of 1 to 4 carbon atoms substituted by phenyl, or phenyl, alkyl of 1 to 4 carbon atoms, or alkyl of 1 to 4 carbon atoms substituted by phenyl, said phenyl, alkyl or phenyl substituted alkyl being substituted by a member selected from the group consisting of hydroxyl, acetoxyl, methoxyl, acetamido, amino or a nontoxic salt thereof, alkylamino of 1 to 4 carbon atoms in the alky moiety, dialkylamino of 1 to 4 carbon atoms in each alkyl moiety and carboxyl.

2. A compound according to claim 1 which has the formula:

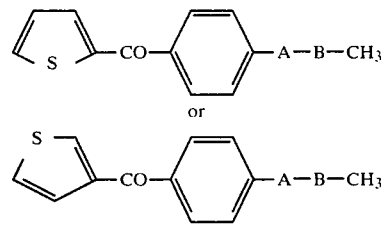

wherein A is —CHRCH$_2$— or —CR=CH— in which R is hydrogen or methyl and B is CO, CHOH or CHOCOR" where R" is alkyl of 1 to 4 carbon atoms.

3. A compound according to claim 1 wherein B is CO or CHOH.

4. A compound according to claim 1 wherein A is —CHCH$_3$CH$_2$—.

5. A compound according to claim 1 which has the formula:

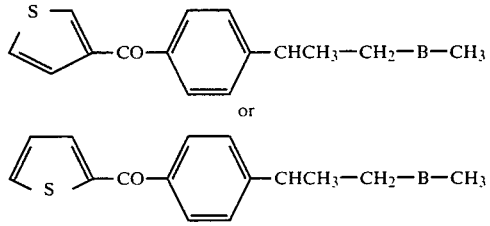

wherein B is CO, CHOH or CHOCOR" wherein R" is alkyl of 1 to 4 carbon atoms.

6. A compound according to claim 5 wherein B is CO or CHOH.

7. A compound according to claim 4 wherein B is CO.

8. A compound according to claim 1 which has a chiral centre which is in R—, S— or RS— form.

9. A compound according to claim 1 in which R is methyl wherein the chiral carbon atom α- to the phenyl ring is in the S— or SR—form.

10. The compound according to claim 1 which is 4-[4'-(2-thienoyl)-phenyl]-pentan-2-one.

11. The compound according to claim 1 which is 4-[4'-(2'-thienoyl)-phenyl]-butan-2-one.

12. The compound according to claim 1 which is 4-[4'-(3'-thienoyl)-phenyl]-butan-2-one.

13. The compound according to claim 1 which is S-4-[4'-(2'-thienoyl)-phenyl]-pentan-2-one.

14. The compound according to claim 1 which is R-4-[4'-(2-thienoyl)-phenyl]-pentan-2-one.

15. The compound according to claim 1 which has a chiral center and is in the form of the R-isomer.

16. The compound according to claim 1 which has a chiral center and is in the form of the S-isomer.

17. A mixture of R and S-isomers of a compound according to claim 1 having a chiral center.

18. A compound according to claim 1 wherein $R^1$ is alkyl of 1 to 4 carbon atoms, phenyl, benzyl, phenylethyl, acetoxymethyl, methoxymethyl, hydroxymethyl, aminomethyl, 2-acetoxyphenyl, 4-methoxyphenyl, 3,4-dimethoxyphenyl or 3,4,5-trimethoxyphenyl.

19. A compound according to claim 1 wherein $R^1$ is methyl, ethyl, n-propyl, phenyl, benzyl, phenylethyl, acetoxymethyl, methoxymethyl, hydroxymethyl, aminomethyl, 2-acetoxyphenyl, 4-methoxyphenyl, 3,4,-dimethoxyphenyl or 3,4,5-trimethoxyphenyl.

20. A compound according to claim 1 wherein B is CO, CHOH or CHOCOR" wherein R" is alkyl of 1 to 4 carbon atoms.

* * * * *